United States Patent
Simon

(10) Patent No.: US 11,468,792 B2
(45) Date of Patent: *Oct. 11, 2022

(54) METHOD AND APPARATUS FOR IDENTIFYING AN INSTRUMENT LOCATION BASED ON MEASURING A CHARACTERISTIC

(71) Applicant: Medtronic Navigation, Inc., Louisville, CO (US)

(72) Inventor: David A. Simon, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 34 days.

This patent is subject to a terminal disclaimer.

(21) Appl. No.: 16/997,325

(22) Filed: Aug. 19, 2020

(65) Prior Publication Data

US 2020/0380890 A1    Dec. 3, 2020

Related U.S. Application Data

(63) Continuation of application No. 14/107,647, filed on Dec. 16, 2013, now Pat. No. 10,755,598, which is a continuation of application No. 12/465,050, filed on May 13, 2009, now Pat. No. 8,608,481.

(51) Int. Cl.
  *G09B 23/28* (2006.01)
  *A61B 5/06* (2006.01)
  *A61B 5/00* (2006.01)

(52) U.S. Cl.
  CPC ............... *G09B 23/28* (2013.01); *A61B 5/06* (2013.01); *A61B 5/7267* (2013.01)

(58) Field of Classification Search
  CPC ............................. A61B 19/5244; A61B 19/56
  USPC ..................... 434/262, 267; 600/300; 705/3
  See application file for complete search history.

(56) References Cited

U.S. PATENT DOCUMENTS

| | | | | |
|---|---|---|---|---|
| 5,305,203 A | * | 4/1994 | Raab | A61B 17/00 606/1 |
| 6,348,058 B1 | | 2/2002 | Melkent et al. | |
| 6,440,067 B1 | * | 8/2002 | DeLuca | A61B 5/389 600/300 |
| 6,450,978 B1 | * | 9/2002 | Brosseau | A61B 90/36 600/595 |

(Continued)

FOREIGN PATENT DOCUMENTS

WO    9628800 A1    9/1996

OTHER PUBLICATIONS

U.S. Appl. No. 12/465,050, now U.S. Pat. No. 8,608,481, filed May 13, 2009, Simon.

(Continued)

*Primary Examiner* — Robert J Utama
*Assistant Examiner* — Sadaruz Zaman
(74) *Attorney, Agent, or Firm* — Harness, Dickey & Pierce, P.L.C.

(57) ABSTRACT

A method to determine the location of an instrument within a patient can be based upon the measuring of a characteristic within the patient and matching the currently measured characteristic with a previously measured characteristic. If the measurements of a characteristic matches in an appropriate or selected manner then a location match can be determined. The characteristic can be any appropriate characteristic and measured in any appropriate way.

13 Claims, 4 Drawing Sheets

(56) References Cited

U.S. PATENT DOCUMENTS

Figure 1:
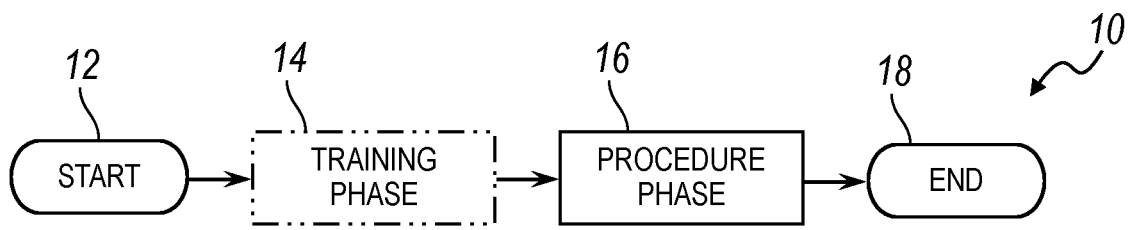

| | | | |
|---|---|---|---|
| 6,546,378 B1* | 4/2003 | Cook | A61B 5/7267 706/12 |
| 6,567,546 B1 | 5/2003 | Eguchi et al. | |
| 7,751,882 B1 | 7/2010 | Helland | |
| 8,007,282 B2 | 8/2011 | Gregorio et al. | |
| 8,208,694 B2* | 6/2012 | Jelonek | G06F 16/58 382/118 |
| 8,262,394 B2 | 9/2012 | Walker et al. | |
| 9,314,192 B2* | 4/2016 | Goris | A61B 5/1118 |
| 10,755,598 B2 | 8/2020 | Simon | |
| 2004/0097805 A1 | 5/2004 | Verard et al. | |
| 2004/0122706 A1* | 6/2004 | Walker | G16H 50/20 705/2 |
| 2004/0141635 A1* | 7/2004 | Liang | A61B 5/4094 382/110 |
| 2006/0008786 A1 | 1/2006 | Feygin et al. | |
| 2006/0052690 A1* | 3/2006 | Sirohey | A61B 8/481 600/420 |
| 2006/0122497 A1 | 6/2006 | Glossop | |
| 2006/0142634 A1 | 6/2006 | Anstadt et al. | |
| 2006/0155263 A1* | 7/2006 | Lipow | A61B 34/77 606/1 |
| 2007/0047794 A1 | 3/2007 | Lang et al. | |
| 2007/0123944 A1* | 5/2007 | Zdeblick | A61N 1/3627 607/17 |
| 2007/0197896 A1* | 8/2007 | Moll | A61B 1/00039 600/407 |
| 2007/0249911 A1 | 10/2007 | Simon | |
| 2007/0282195 A1* | 12/2007 | Masini | A61B 90/98 600/424 |
| 2008/0020361 A1* | 1/2008 | Kron | G09B 5/02 434/262 |
| 2008/0077158 A1* | 3/2008 | Haider | A61B 17/1703 606/130 |
| 2008/0214922 A1 | 9/2008 | Hartmann et al. | |
| 2008/0269596 A1* | 10/2008 | Revie | A61F 2/4603 600/424 |
| 2008/0281234 A1* | 11/2008 | Goris | A61B 5/7253 600/595 |
| 2008/0292153 A1* | 11/2008 | Binnig | G06T 7/0012 382/128 |
| 2009/0264727 A1 | 10/2009 | Markowitz et al. | |
| 2009/0264752 A1 | 10/2009 | Markowitz et al. | |
| 2009/0264778 A1* | 10/2009 | Markowitz | A61B 5/053 600/508 |
| 2009/0265128 A1* | 10/2009 | Markowitz | A61B 34/20 702/94 |
| 2010/0035222 A1* | 2/2010 | Kukora | G09B 23/28 434/262 |
| 2010/0130832 A1 | 5/2010 | Lang et al. | |
| 2010/0167248 A1 | 7/2010 | Ryan | |
| 2010/0291521 A1 | 11/2010 | Simon | |
| 2013/0172902 A1* | 7/2013 | Lightcap | A61B 5/4836 606/130 |
| 2015/0320500 A1* | 11/2015 | Lightcap | A61B 34/76 606/96 |
| 2017/0173262 A1 | 6/2017 | Veltz | |
| 2020/0352518 A1* | 11/2020 | Lyman | A61B 5/7257 |

OTHER PUBLICATIONS

U.S. Appl. No. 14/107,647, now U.S. Pat. No. 10,755,598, filed Dec. 16, 2013, Simon.
Bishop, Christopher, "Pattern Recognition and Machine Learning," Springer Science+Business Media, LLC, 2006, pp. 1-749.
Communication pursuant to Article 94(3) EPC in corresponding European Application No. 10719706.3-1666 dated Mar. 15, 2016.
Duda, et al., "Pattern Classification," 2nd Edition.
Duda, et al., "Pattern Classification," 2nd Edition, 2001.
European Communication pursuant to Article 94(3) dated Dec. 28, 2016 for European Application No. 107197063 corresponding to PCT/US2010/034717 claiming benefit of U.S. Appl. No. 12/465,050, filed May 13, 2009.
European Office Action dated Jul. 26, 2017 in corresponding European Application No. 10719706.3.
Hertz et al., "Introduction to the Theory of Neural Computation".
Hertz et al., "Introduction to the Theory of Neural Computation," 1991.
International Preliminary Report on Patentability and Written Opinion dated Nov. 24, 2011 for PCT/US2010/034717 claiming benefit of U.S. Appl. No. 12/465,050, filed May 13, 2009.
International Search Report and Written Opinion dated Sep. 14, 2010, for PCT/US2010/034717 claiming benefit of U.S. Appl. No. 12/465,050, filed May 13, 2009.
Theodoridis et al., "Pattern Recognition," 3rd Edition.
Theodoridis et al., "Pattern Recognition," 3rd Edition, 2006.

* cited by examiner

30a

A) NAVIGATE A CATHETER TO A LOCATION IN ONE or MANY PATIENT(S)
   1) A POPULATION OF PATIENTS
   2) A SINGLE PATIENT ACQUIRED PRIOR TO
      THE RELEVANT PROCEDURE (e.g. DIAGNOSTIC INFORMATION)

B) ACQUIRE INFORMATION AT SELECTED LOCATION, e.g.
   i) INSTRUMENT MOTION: ACCELERATION, VELOCITY
   ii) FLUID MOTION – DIRECTION, TURBULENCE, VELOCITY
   iii) ELECTRICAL ACTIVITY – e.g. ELECTROGRAM, ELECTROPHYSIOLOGY
   iv) PRESSURE: FLUID, TISSUE, PULSATIVE
   v) TISSUE STIFFNESS AND/OR DENSITY (e.g. CATHETER PUSH INTO TISSUE)

FIG. 2B

30b

A) ACQUIRE NON-INVASIVE INFORMATION OF A LOCATION OF ONE OR MORE PATIENT(S)
   i) CT
   ii) MRI
   iii) US (WITH OR WITHOUT DOPPLER)
   iv) FLUOROSCOPY 1) A POPULATION OF PATIENTS
   2) A SINGLE PATIENT ACQUIRED PRIOR TO
      THE RELEVANT PROCEDURE (e.g. DIAGNOSTIC INFORMATION INCLUDING CT)

B) ANALYZE NON-INVASIVE INFORMATION AT SELECTED LOCATION, e.g.
   i) INSTRUMENT MOTION: ACCELERATION, VELOCITY
   ii) FLUID MOTION – DIRECTION, TURBULENCE, VELOCITY
   iii) ELECTRICAL ACTIVITY – e.g. ELECTROGRAM, ELECTROPHYSIOLOGY
   iv) PRESSURE: FLUID, TISSUE, PULSATIVE
   v) TISSUE STIFFNESS AND/OR DENSITY (e.g. CATHETER PUSH INTO TISSUE)

FIG. 2C

METHOD AND APPARATUS FOR IDENTIFYING AN INSTRUMENT LOCATION BASED ON MEASURING A CHARACTERISTIC

CROSS-REFERENCE TO RELATED APPLICATIONS

This application is a continuation of U.S. patent application Ser. No. 14/107,647 filed on Dec. 16, 2013, which is a continuation of U.S. patent application Ser. No. 12/465,050 filed on May 13, 2009, now U.S. Pat. No. 8,608,481 issued on Dec. 17, 2013. The entire disclosures of the above applications are incorporated herein by reference.

FIELD

The present application relates to a method and apparatus of identifying a location of an instrument relative to a patient, and particularly to identifying a location of an instrument relative to a patient based upon measurements taken at the position of the instrument.

BACKGROUND

This section provides background information related to the present disclosure which is not necessarily prior art.

A procedure can be performed on a patient using various techniques and instrumentation. For example, ablation or stent implantation can be performed relative to a particular and selected portion of a patient's heart. Various techniques are required to determine a location of an instrument prior to performing a particular procedure.

For example, it is generally selected to substantially precisely locate the ablation instrument to ensure appropriate ablation of an appropriate portion of the anatomy. X-ray images may be acquired to determine the location of an instrument in a patient prior to performing an ablation procedure. Arrhythmias of a patient's heart can be treated with an ablation of a particular and specific anatomical location within a patient's heart. Generally, the selected results, such as an elimination of an arrhythmia, are achieved only when the particular anatomical location is ablated.

Determining the location of the instrument can also be performed with generally known navigation instruments and procedures. The navigation instrument and procedures, however, may also require additional equipment and specialized training. The navigated instruments may require additional capital equipment and greater size. Alternatively, a procedure may be done in an open manner. Thus, navigation or position determination is done by the surgeon through direct visualization. Open procedures, however, may be more traumatic to patients.

SUMMARY

This section provides a general summary of the disclosure, and is not a comprehensive disclosure of its full scope or all of its features.

A method to determine the location of an instrument within a patient can be based upon the acquisition and measuring of specific characteristics within the patient. The characteristic can be a feature or characteristic that is extracted from a data. For example, training measurements can be made of a patient or population of patients at a specific location within the patient. A specific location can include, as an example, a superior vena cava junction into the right atrium. Measurements of characteristics can lead to acquisition of information of a patient or population of patients regarding the specific location. Characteristics can include motion or movement, pressure, pulsative pressure, electrograms, or other information. The acquired training information can then be used to create a database that can be accessed to identify when the location is reached by an instrument based upon matching pre-acquired characteristic measurements with current or procedure measurements of the characteristics. The pre-acquired characteristic can be used to generate a training or pre-acquired fingerprint and the procedure measurements can be used to generate a procedure fingerprint. An algorithm or system can determine the probability of a match between the training fingerprint and the procedure fingerprint.

According to various embodiments, a method of locating an instrument can include a training phase and a procedure phase. The training phase can include selecting a training location; identifying a characteristic at the training location; acquiring a training datum by measuring the characteristic at the training location in a training instance; and determining a pattern in the training datum at the training location. The procedure phase can follow the training phase and include acquiring a procedure datum by measuring the characteristic during a procedure at a procedure location; and determining if the procedure datum matches the determined pattern.

According to various embodiments a method of locating an instrument can include a training phase. The training phase can include selecting a training location; selecting a characteristic at the training location; obtaining a set of characteristic training data by measuring the characteristic at the training location in a training instance; determining a pattern in the training data at the training location; and saving the determined pattern as a predetermined pattern. A procedure or intervention may use the predetermined pattern to identify a location of an instrument.

According to various embodiments a system of locating an instrument can include an input instrument operable to be positioned into an anatomy to input data to the memory system. A first classifier can classify the input data into a classification from the input instrument and a processor can determine a location of the input instrument based upon the classification of the input data. An output can be made to output the location to a user.

The information can be acquired with an instrument positioned within a patient, such as a catheter. Other techniques can also be used to acquire the information of the characteristics within the patient. For example, image data can be used to acquire characteristic information at a particular location of the patient. Magnetic Resonance Image (MRI) or computer tomography (CT) data can be used to determine certain specific characteristic information that can then be used to determine measurable data, such as characteristics measured with an instrument. For example, image data can be analyzed to determine a pulsative pressure, heart wall, or organ motion at a specific location.

Instruments can then be used to make procedure or current measurements of the characteristics. According to various embodiments a catheter can include a motion sensor (e.g. an accelerometer) for measuring motion of a portion of a patient. According to various embodiments, a catheter can include a pressure sensor that measures pressure as it is moved or positioned within a patient. As the pressure is measured, such as a pulsative pressure, the measured pulsative pressure can be compared to the database of pulsative pressures to identify when the catheter is positioned at a specific physical location within the patient based upon matching the pulsative pressure currently measured and that within the database. It will be understood that any appropriate comparison can be used to determine if a match is found.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2A:
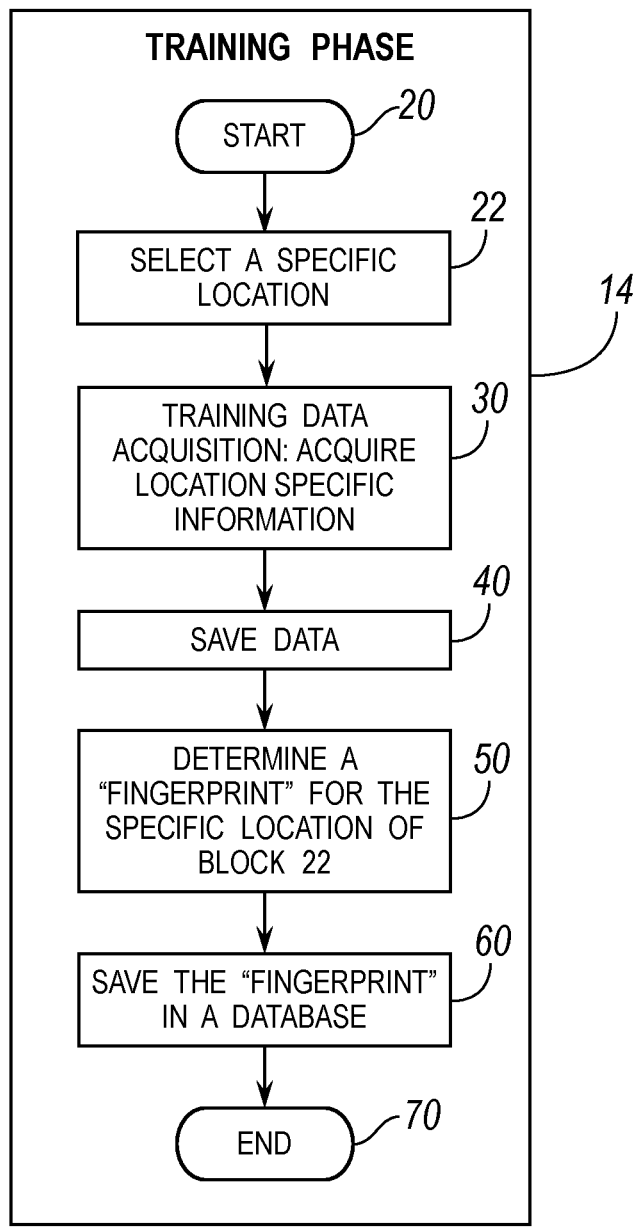
Figure 3:
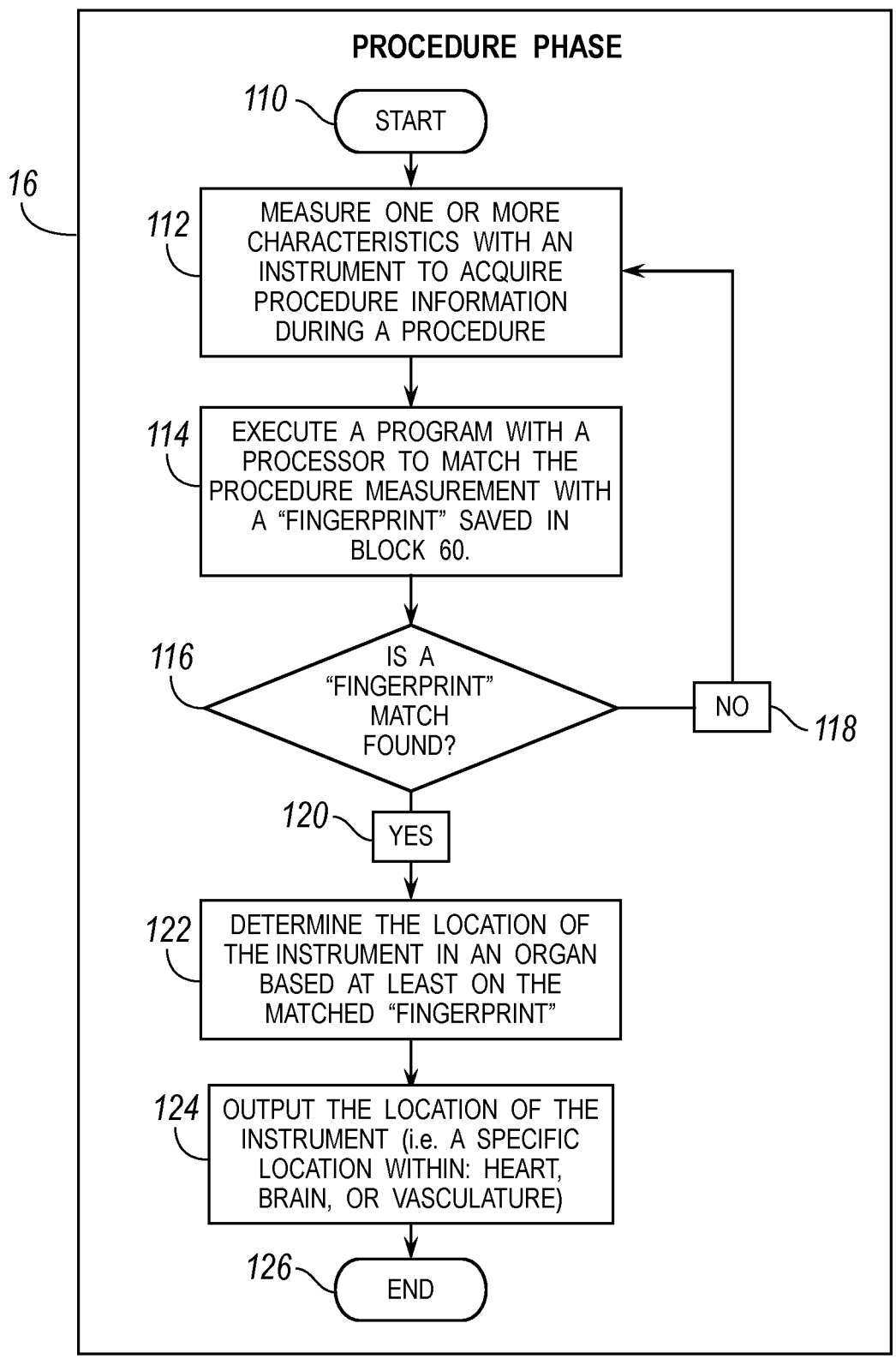
Figure 4:
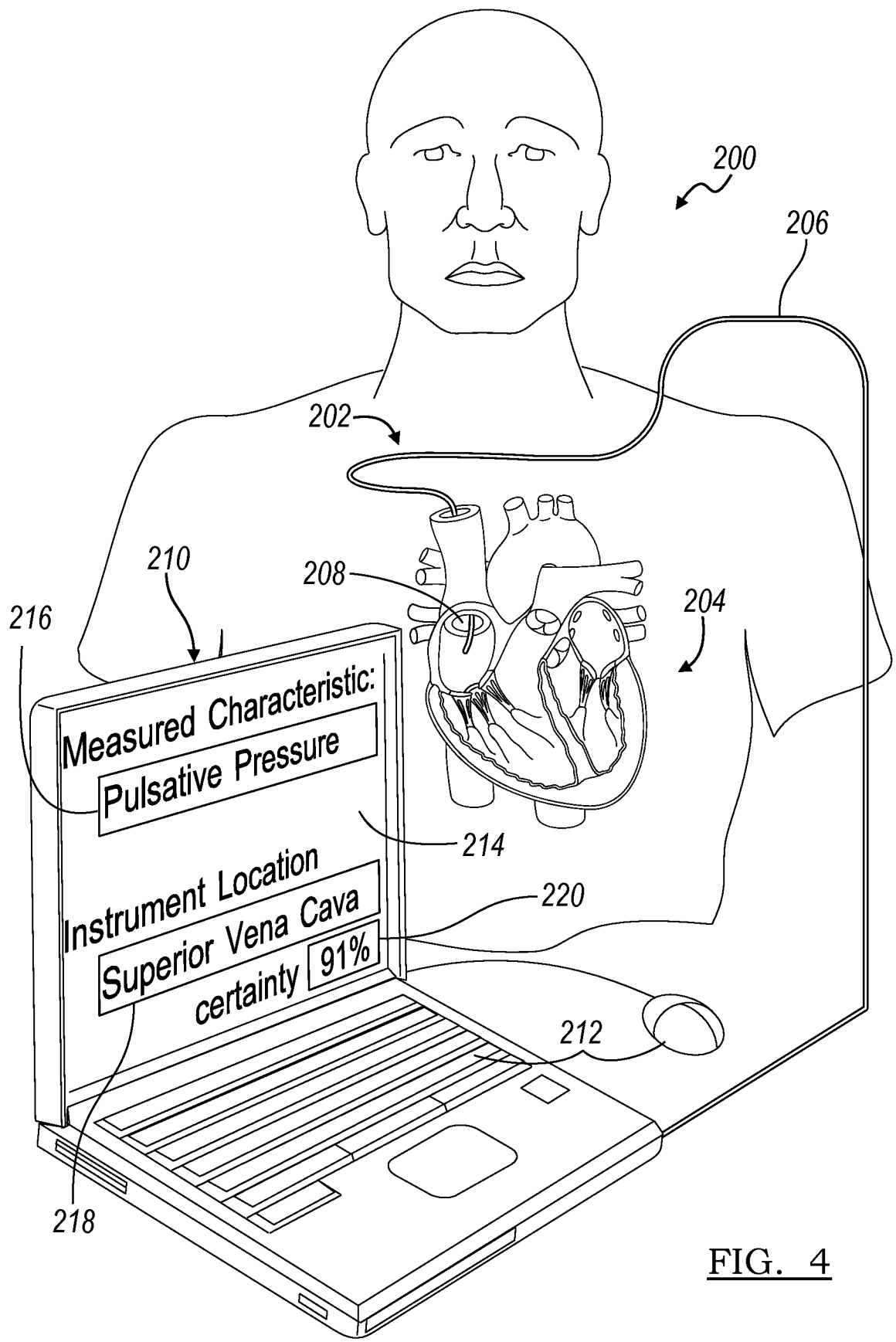

FIG. 1 is a flowchart of a procedure, according to various embodiments;

FIG. 2A-C are flowcharts of a training process, according to various embodiments;

FIG. 3 is a flowchart or a procedure process, according to various embodiments; and FIG. 4 is a schematic environmental view of a position identification system, according to various embodiments.

Corresponding reference numerals indicate corresponding parts throughout the several views of the drawings.

DETAILED DESCRIPTION

Example embodiments will now be described more fully with reference to the accompanying drawings. It will be understood that although the following description may relate specifically to an identified characteristic within a heart of the patient, that the method and instrumentation disclosed herein can be used in any appropriate location within the patient. For example, instruments can be positioned within a heart, a liver, a pulmonary region, a neurological region, or other appropriate portions of the patient. Accordingly, the description relating to a cardiac procedure herein is merely exemplary and not intended to limit the scope of the current disclosure or the included claims.

With reference to FIG. 1, a system or process 10 is illustrated in a flow chart. The system 10 can include in start block 12. After start block 12, a training phase can occur in block 14. The training phase, as discussed further herein, generally relates to making training measurements to acquire information or data of a characteristic at a specific location. The information can be used to train a computer system, neural network, and/or algorithm or for creating a database based upon the acquired characteristic information. Following the training phase, a procedure phase in block 16 can occur. The procedure phase in block 16 can include performing a procedure on a patient based at least in part upon the training phase in block 14. After the procedure, the system 10 can end in end block 18.

It will be understood, the system 10, including the training phase in block 14 and the procedure phase in block 16, need not occur sequentially at a given time. For example, the training phase in block 14 can occur using a plurality of patients or over an extended period of time to train a system (such as a classifier) or generate a database. The training phase in block 14 can occur at any appropriate time to generate an appropriately trained system. The procedure phase in block 16, therefore, can occur at any appropriate time after the training phase in block 14.

In addition, it will be understood that the training phase in block 14 is not always required to proceed to the procedure phase in block 16. For example, once the training phase in block 14 is completed and a database or other appropriate system has been taught or created the procedure can proceed any number of times. Thus, to perform a procedure according to the procedure phase in block 16, a training phase in block 14 need not always immediately proceed the procedure phase in block 16.

As discussed further herein, the training phase in block 14 can include the acquisition of training data relating to a population of patients. Accordingly, the data can be statistically analyzed or classified in the training phase in block 14. The training phase in block 14 can also include generating a fingerprint or pattern based upon the acquired information. The fingerprint can be imbedded in a classification system that can include feature extraction to allow for classification of a procedure datum acquired with a procedure measurement during a procedure. After this occurs, the procedure phase in block 16 can be performed using the fingerprint from the training system in block 14.

The training phase in block 14 can occur based upon a particular patient, such as the patient upon which the procedure in block 16 is performed. Accordingly, the training phase in block 14 can be contemporaneous or close in time to the procedure phase in block 16. Therefore, one skilled in the art will understand the training phase in block 14 can occur at any appropriate time relative to the procedure phase in block 16.

With initial reference to FIG. 2A, the training phase 14 is illustrated in greater detail. The training phase in block 14 can include a plurality of steps or sub-procedures to appropriately train a system or generate a database or fingerprint. The fingerprint that is generated can be a single datum or a series of data or pattern that is generated. The pattern can be stored in a database or a plurality of fingerprints can be stored in a database. Alternatively, a single file or accessible memory portion can be used to store the fingerprint rather than a database.

The training phase 14 can begin in start block 20. After starting the training process, a specific location can be selected in block 22. The specific location can be any appropriate location in a patient or any other appropriate position. The location can be specifically known or determined with imaging navigation, or other location identification techniques. Data acquisition, such as acquiring information regarding a specific location, can occur in block 30. As discussed further herein, various data acquisition techniques can be used to acquire the location specific information. The location specific information can be at locations within any appropriate portion of an anatomy. For example, the location of specific information can be within a heart, brain, vasculature, pulmonary system, or any appropriate specific location. The specific location, as discussed further herein, can include the location of the superior of vena cava juncture with the right atrium. In addition, as also discussed further herein, the type of data acquired in the training data acquisition in block 30 can be any appropriate data. As a brief example, appropriate data can include electrograms, pulsative pressures, acceleration, velocity, static or dynamic position, or other selected data.

After the training data is acquired in block 30, the data can be saved in block 40. Saving the data in block 40 can be any appropriate saving procedure. For example, the data can be saved to a network memory system, a volatile memory, a non-volatile memory, or any appropriate memory. Regardless, the acquired information in block 30 can be saved in block 40. Additionally, the data saved in block 40 can be accessed for various procedures.

The data that is saved in block 40 can simply be added to previously acquired data or used to replace the previously acquired data. For example, in a series of patients each patient can be used to acquire data and all of the data can be saved. Alternatively, a series of data gathering procedures can be performed on a single patient or group of patients. It can be selected to only save a portion of the acquired data.

After the data is acquired in block 30 and saved in block 40, determining a fingerprint for the location can occur in block 50. As discussed above, the data acquired is for a specific location. Therefore, the data acquired in block 30 regarding the specific location can be used to generate or determine a fingerprint, also referred to as a training fingerprint, for the specific location selected in block 22. The fingerprint, as further discussed herein, can then be compared to features or characteristics measured during a procedure. The procedure measurements can be compared to the fingerprint generated from the training data. Thus, the procedure measurements can be referred to as a procedure fingerprint. A program or algorithm, such as a neural network discussed herein, can compare the training fingerprint to the procedure measurements or fingerprint.

The determination of the fingerprint or the fingerprint can be any appropriate determination. Determining the fingerprint can involve statistical based analysis, neural networks, or probabilistic based models. As discussed herein, the fingerprint can include a model or pattern that is found or determined based upon an analysis using an algorithm or with other types of review. Also, the fingerprint can be identified by executing an algorithm by a processor or with manual determination, or a combination of both automatic and manual determination. For example, a fingerprint can include a probable pulsative pressure or electrogram that is present at the SVC junction. The probabilistic pulsative pressure can be based on measurements of one patient or of a plurality of patients. If the pulsative pressure acquired in block 30 is based upon a population of patients, a variation within the population of patients can be accounted for when determining the fingerprint in block 50.

The data acquired in block 30 can be analyzed according to appropriate techniques, such as those disclosed in Duda et al., Pattern Classification, $2^{nd}$ Ed., John Wiley & Sons, 2001; and Theodoridis et al., Pattern Recognition, $3^{rd}$ Ed., Elsevier, 2006; Introduction to the Theory of Neural Computation, Hertz, John A., et al., Westview Press, 1991; all incorporated herein by reference. The analytical, computational, and combinative techniques can be used to identify relationships amongst the acquired and saved data, from blocks 30 and 40, to determine the fingerprint in block 50 and/or compare newly acquired data with a fingerprint to determine a match or a probability of a match. In addition, it will be understood, that a manual analysis can be used to determine a fingerprint of the saved data in block 40. The techniques can include identifying features in the data that can be used to classify later acquired data.

The fingerprint can be used with any appropriate system, such as a neural network or statistical analysis system or algorithm to find a match to or a probability of a match to a later measured characteristics. The characteristic can also be referred to as a feature that is present in a set of data, such as training data. The fingerprint, generated from the feature, can be manually generated, automatically generated, or generated based on a combination of automatic and manual inputs. The fingerprint can also be referred to as an input into the system or algorithm that is to determine a match with the later measured characteristic.

The fingerprint may include only one feature or more than one feature. If more than one feature is included in the fingerprint, the features may be blended into a single fingerprint or left as separate features within the fingerprint. If the fingerprint is a blended fingerprint it may include averaged data or data that is manipulated over time. If the features are left separate the features can be saved and accessed as distinct and separate points with or without relation to time or other dynamic measurements.

An example of a blend of multiple features in the fingerprint may include a measured position (but may also include a pulsative pressure, velocity, etc.) during a physiological cycle, such as a cardiac cycle. The measured position can be blended with the cardiac cycle to generate a blended curve indicating the change in position over the time of the cardiac cycle. Also, the curve could be based on an average of several cardiac cycles and several subjects, as discussed herein. The blended curve could then be matched to a patient or procedure curve.

When the features are selected to be separate, the measured position could be measured or determined at distinct points in the cardiac cycle. The measured positions can be averaged over several cardiac cycles and/or population, as discussed herein. Each of the measured points and their relation to the cardiac cycle could be used to compare to a procedure measurement. Thus, rather than a curve or blend of the position and the cardiac cycle, the two are kept separate for generation of the fingerprint.

It will also be understood that the use of the phrase "fingerprint" is not intended to limit or identify an identity in the data. The phrase or term fingerprint is merely understood to identify a model or feature that is used as an input for the classification system that can be compared to procedure measured characteristic data in the procedure phase 16. It will be understood that fingerprint used herein, unless specified otherwise, does not relate to a literal print left by a finger. Rather, fingerprint is directed to a pattern that is generated or recognized from the acquired data.

Once the fingerprint has been determined in block 50, it can be saved in a database in block 60. The saving of the fingerprint in a database can be any appropriate saving procedure, similar to the saving of the data in block 40. Also, a database need not be created, but only a file in an accessible data format. It will be understood, however, that the database may be accessed for various procedures, such as during the procedure phase 16. In addition, various instruments can be used to collect or measure data relating to a patient during the procedure phase in block 16, which can be interconnected with a processor and/or classifier system. The processor system can access the database into which the fingerprint is saved in block 60 for analysis in determination of the match to a fingerprint, as discussed further herein. The processor system may also be a classifier system or algorithm operable to classify incoming data based upon the fingerprint, also the classifier may be a single or separate system. The training phase can then end in block 70.

With reference to FIG. 2B, exemplary data acquisition or techniques is illustrated in block 30*a*. The exemplary data acquisition in block 30*a* can be used to acquire data in block 30, in FIG. 2A. Data acquisition can be data acquired from any appropriate selected source. For example, data can be acquired through an invasive procedure. Summarized in block 30*a*, a catheter can be navigated to a location within one or more patients.

A catheter can be navigated within the patient to acquire information regarding the one or more patients to acquire the data for block 30 of the training process 14. According to various embodiments, an invasive procedure, as noted in block 30*a*, can include moving a catheter within 1) patients in a population of patients or 2) within a single patient. If the catheter is moved relative to a population of patients, a set of data points can be acquired for each patient which can include a plurality of data points. This allows multiple sets of data points regarding each of the patients to be acquired. All of these data points can be saved for determining a fingerprint in block 50. The data can include any appropriate data, such as that discussed below, for one or many locations within each patient of the population. A study group of patients can be interrogated with the catheter, or other appropriate invasive instrument, to measure the characteristic and acquire training information at one or more locations within each patient in the population.

The training information can then be saved and used to determine a fingerprint without any patient identifying information being acquired and saved with the saved acquired information, unless selected, as discussed below. For example, a pulsative pressure can be measured at a selected point within the patient. That particular pulsative pressure, either one or multiple pressures at one point, can be saved or averaged. A pulsative pressure at the same location, either a single or average pulsative pressure from each of the patients in the population can also be acquired and saved. This information need not be associated with any other information regarding the patient, such as name, age, other conditions, or the like. Even if other information is acquired, it may be simply to clarify or provide additional information for the fingerprint created in block 50.

The information can, however, also be associated with specific patient information. For example, if a pulsative pressure is taken in a patient with an atrial fibrillation, that information can be associated with the pulsative pressure measured in the patient of the population. In addition, a separate database or fingerprint can be created for patients with particular conditions. For example, electrograms of a population with atrial fibrillation or with a heart attack can be generated to create illness specific fingerprints. Thus, patient specific information can also be used to help generated or identify the fingerprint. This information can also be population specific, as opposed to individual specific. For example, a population of individuals having had at least one infarction can be used to generated a database or fingerprint.

It may also be selected to acquire information regarding a single patient. For example, during an invasive procedure, such as an initial procedure, information can be acquired of the patient, including pulsative pressures, electrograms, or the like. During a subsequent procedure, this information can be used regarding the same specific patient. For example, during implantation of a stent in a vasculature of a patient, information can be acquired of that patient and a fingerprint determined. During a second procedure, such as the positioning of a second stent or a angioplasty, the patient specific fingerprint can be used, as discussed further herein, to identify the location of a catheter during the second procedure. Therefore, rather than requiring an invasive procedure on more than one patient, information regarding a single patient can be used to identify the same specific locations within the patient, according to various embodiments.

Whether acquired in a single patient or a population, the information acquired in block 30*a* can be any appropriate information. It can be directly measured or inferred from the instrument positioned within the patient during the invasive procedure noted in A). The information acquired in B) in block 30*a* can be any appropriate information regarding a characteristic. For example, i) instrument motion can include acceleration, velocity, position, or other information. For example, a position identification or tracking portion, such as those disclosed in U.S. Pat. App. Pub. No. 2004/0097805 (U.S. patent application Ser. No. 10/619,216) entitled, "NAVIGATION SYSTEM FOR CARDIAC THERAPIES" including an electromagnetic navigation or tracking system and U.S. Pat. App. Pub. No. 2009/0264752 (U.S. patent application Ser. No. 12/117,537) entitled, "METHOD AND APPARATUS FOR MAPPING A STRUCTURE", including the navigation or mapping system such an electrical potential system, both incorporated herein by reference, can be associated with the instrument to determine acceleration or velocity of the instrument by measuring displacement of the instrument over time.

When an instrument is positioned within a superior vena cava, velocity of the instrument moving within the superior vena cava can be measured. Also, the information can be generated relating to various patient rhythms or cycles. For example, motion during different and specific portions of the cardiac cycle can be measured. The motion at different parts of the cycle can also be used to generate the fingerprint. Thus, a fingerprint, as discussed herein, can include more than one type of information. According to various embodiments it can include motion at a specific time in a cardiac cycle. Though motion at a specific time in a respiration cycle or other cycles can be used. This information can be acquired and saved in block 40.

Additional or alternative characteristics about which information is acquired can be ii) fluid motion. Fluid motion can be motion measured of the fluid such as the direction, turbulence, velocity or other fluid motion information. Sensors on the instrument being positioned within the patient can measure the fluid motion relative to the instrument. The information regarding the fluid motion can be saved in block 40.

Additional or alternative information can be acquired regarding the characteristic of iii) electrical activity. Electrical activity can include electrical activity that is measured with various portions, such as an electrode on the instrument. Information can be acquired about electrograms, electrophysiology, comparative electrophysiology, or other electrical activity information. For example, the instrument can include an electrode that can measure a potential that is generated within a muscle or tissue and this data can be saved in block 40.

Additional or alternative characteristics can include (iv) pressure information. Pressure information can include fluid pressure, tissue pressure, pulsative pressure, or other pressure measurements. For example, pressure of a fluid on the instrument can be measured with an appropriate instrument. These instruments can include a bladder or balloon can be inflated with a non-compressible material and pressure on this balloon can be measured with an appropriate pressure meter. Pulsative pressure can include instantaneous pressure changes measured on the balloon within the patient. Again, the data regarding pressure can be saved in block 40.

Further or additional alternative characteristics can include (v) tissue stiffness or density. For example, a pressure sensor can be associated with a catheter and the catheter can be pressed into tissue to acquire information regarding the stiffness. Also, an ultrasound (e.g. ultrasound catheter) can be used to determine or estimate tissue stiffness.

The information acquired in (B) can be any appropriate information and need not be limited to the exemplary types of information listed in block 30*a*. Various sensors that might be incorporated or associated with a catheter or other invasive instruments can be used to acquire any information regarding a characteristic at a particular location within the patient. Nevertheless, as the information is acquired, a position of the instrument is also known relative to the patient, including or at the specific location for which the fingerprint is being developed. The position of the instrument can be determined via a position sensor on the catheter or associated with the catheter, imaging of the patient and the instrument, or any other appropriate or known location or determination technique or procedure. For example, a position sensor can be associated with the catheter as it is positioned within a patient of the population or a single patient, as discussed above. The training information about the characteristic can then be acquired and associated with the known position of the catheter within the patient. When saving the training data within block 40, it can then include both a known location of the instrument and the acquired training information that is measured with the instrument. Accordingly, the data saved in block 40 that is used to determine the fingerprint in block 50 can include both known locations and the acquired information. As discussed further herein, the acquired information and the known location of the acquired information can be used to create a fingerprint for various purposes.

Turning to FIG. 2C and block 30*b*, the acquisition of training information in block 30 of the training process 14 can include non-invasive acquisition techniques. For example, information can be acquired or produced from various imaging techniques, including (i) CT, (ii) MRI, (iii) ultrasound (US), (iv) fluoroscopy, or other appropriate imaging techniques. Additionally, non-invasive information can be acquired via external sensing devices, such as an electrocardiogram device. The non-invasive training information can be acquired again, from a 1) population of patients or 2) single patient. The population of patients can be any appropriate population of patients that is subjected to an interrogation by non-invasive information gathering techniques. Further, the single patient can be a single patient on which a procedure is to be performed and the non-invasive techniques can be used to interrogate the single patient. Regardless of whether a population of patients or a single patient is used to acquire in the training information, the information can be saved in block 40. As discussed above, in relation to the information acquisition in block 30, the information can be gathered as individual points, averaged, associated or not associated with any other patient information, or any appropriate data acquisition model.

Regardless of whether a single patient or population of patients is used to acquire the data, the non-invasive information can be analyzed for a particular or multiple particular measurements to define or obtain the information (B) about a characteristic. As discussed above, the information that is acquired can be any appropriate information, and can include (i) instrument motion, (ii) fluid motion, (iii) electrical activity, (iv) pressure, (v) tissue stiffness or density, or any other appropriate information. The information that is acquired from the non-invasive interrogation technique can be the same or different information from that acquired with the instrument in block 30*a*. Regardless, the information that is obtained through the analysis of the non-invasive information or interrogation technique can be known by analysis of the non-invasive information. For example, a doppler ultrasound (US) can be used to measure fluid motion. The location of the fluid motion is known due to its relative position to the anatomy in the imaging data. Other non-invasive information techniques can also identify the location for which the information is obtained.

Regardless of the procedure for the acquiring the training data in block 30, the data can be saved in block 40, as illustrated in FIG. 2. A fingerprint can then be determined for the specific location and the fingerprint can be saved in the database, as also illustrated in the training process in FIG. 2. Once the fingerprint is saved in the database, or any other appropriate accessible system, the fingerprint can be used during the procedure 16, illustrated in detail in FIG. 3. Briefly, because the fingerprint relates to a specific and known location within a subject, such as a patient or system, making a procedure measurement that matches the saved or predetermined fingerprint can be used to determine the location at which the procedure measurement is made. An instrument can make a procedure measurement of a characteristic in the patient and the procedure measurement can be analyzed to determine a match to the saved fingerprint. In other words, during the training process location of an instrument was known and the fingerprint was determined based upon the data acquired at that location. Matching a procedure measurement to a fingerprint allows the determination that the measurement is made at the same location as it was during the training procedure. The determination can be made automatically, such as with a processor, or manually, by a user.

The procedure 16 can be followed to perform a procedure relative to any portion of a patient, such as within or near the heart of the patient, a brain of the patient, a vasculature of the patient, or any other appropriate portion. The procedure performed in procedure block 16 can include both making a measurement to be matched to the fingerprint and performing a further selected intervention or procedure at a selected location. For example, a stent can be implanted, an ablation can be performed, a lead can be implanted, and other appropriate procedures performed. It will be understood, that the procedure 16 can be used to identify the location of an instrument at any appropriate location for which a fingerprint has been predetermined and any appropriate procedure can then be carried out.

In addition, it will be understood that the training procedure 14 in FIG. 2A and the procedure 16 in FIG. 3 can be used for any appropriate non-surgical or non-medical procedure. For example, the training process 14 in FIG. 2A can be used to identify a fingerprint for a particular location in any of selected dynamic or static system. In a mechanical system an exploratory tool or manipulative tool can be moved within a casing to acquire or measure information regarding portions of the mechanical system within the casing. The measurements or information can be used to identify specific locations within the casing and this information can be used to determine whether or not the manipulative tool is positioned at an appropriate location for performing a procedure on the mechanical system. The techniques could be used to identify positions for servicing a mechanical system, positions for assembling or fabricating a mechanical system or any other appropriate procedure. As a specific example, while building an airframe or a wing assembly for an airframe, small constrained places may later need to be threaded with electrical wiring, insulated, welded, riveted, etc. A location identification system can be used to identify whether an instrument is at an appropriate location for performing a procedure, such as welding, riveting or the like.

The procedure 16 can begin at the start block 110. The start block can include, for example, forming an incision in a patient, moving an instrument relative to a portion of the patient, or appropriate system, forming a burr hole in a patient, or any other appropriate starting procedures. It will be further understood, that although the following description may be directed to a specific anatomical procedure that the procedure 16 can be used in any appropriate situation or procedure, such as for performing a procedure on a mechanical system.

After starting a procedure of block 110, measuring one or more characteristics with an instrument during the procedure 16 can occur in block 112. Measuring the characteristic during a procedure can be measuring any appropriate characteristic, such as the characteristic for which training information was acquired in block 30 through any appropriate technique, such as the techniques described in blocks 30a and 30b. The training information previously acquired regarding the characteristic can be similar to a procedure information of the characteristic taken in block 112. For example, an instrument positioned within a patient can be used to measure a pressure, such as a pulsative pressure, within the patient. The measurement of the characteristic can include a measurement of the pulsative pressure within the patient that is similar to a pulsative pressure of the acquired data in block 30. In other words, if pulsative pressure was the training information that was used to determine the fingerprint the procedure information can be measuring a pulsative pressure as well. A determined match between the procedure measured pulsative pressure and the fingerprint based on the training measurement can be used to identify a location of the instrument making the procedure measurement.

Once one or more procedure measurements of a characteristic have been made, a program and/or algorithm can be executed with a processor to match the procedure measured characteristic with the fingerprint saved in block 60. As discussed above, the fingerprint can be any appropriate fingerprint and a comparison can be made based upon any appropriate rule or via a classification. As discussed above, appropriate rules can include algorithms or computer programs that can be executed to determine whether a match is found between the fingerprint and the measured characteristic. For example, the pulsative pressure fingerprints can include a pulsative pressure or a pulsative or change in pressure over time or physiological cycle, such as an electrocardiogram (ECG). During the execution of the program, the program can determine whether the procedure pulsative pressure measured in block 112 is similar to the fingerprint saved in block 60. The comparison in block 114 can include an appropriate comparison including a Bayesian classifier or a linear discrimination. It will be understood, therefore, that comparing the measured characteristic need not only include determining whether an exact match has been made between the measured characteristic and the fingerprint or any of the particular saved data in block 40. In fact, a comparison can determine whether the characteristic measured is close enough to the fingerprint to determine or identify a match. The comparison in block 114 can also determine a certainty of the match.

A decision block 116 includes determining whether a fingerprint match has been found. A fingerprint match may not be found and the NO routine 118 may be followed to measure one or more characteristics at the same or different location again. Again, the fingerprint generated and saved in the database in block 60 can be generated based upon appropriate rules. Accordingly, the fingerprint saved in the database in block 60 may not be a single or discreet numerical value or measurement. It may include a range or characteristic determination. Therefore, further or additional measurements may be necessary to determine a match. Also, the fingerprint may be based on more than one type of measurement such as pressure and an electrogram.

In decision block 116, if a match to the fingerprint is found then the YES routine 120 can be followed to determine the location of the instrument in an organ or portion of the patient based at least on the match of fingerprint in block 122. As discussed above, the fingerprint is generated and based upon the acquisition of the data in a particular location within the patient, or other appropriate system such as a mechanical system. Accordingly, a fingerprint of the characteristic, including pulsative pressures, tissue densities, fluid motion, or the like, are related to a particular location within the patient. Accordingly, a pulsative pressure fingerprint X and the measured pulsative pressure X' are compared to one another. If an appropriate relation or match is found it can be used to identify the location of the instrument, or at least a portion of the instrument acquiring the measurement for a characteristic of block 112, within the patient.

Outputting the location of the instrument can be done in block 124. The specific location of the instrument can be within the heart, the brain, the vasculature, or any other appropriate location. For example, a particular pulsative pressure or fluid motion can be used to generate a fingerprint that is saved in database 60 for the superior vena cava, the OS between the right and left atriums, or other appropriate specific locations within the patient. Accordingly, the specific location of the instrument within the patient can be identified without an additional invasive procedure, additional navigational systems, imaging systems, or other systems in addition to the instrument that is in the patient and used to measure the characteristic of block 112.

Accordingly, a catheter that is positioned within the patient can be used to measure a pulsative pressure. That pulsative pressure can then be compared to a fingerprint. The fingerprint relates to a specific location so that when a match is found between the procedure measured pulsative pressure in block 112 and the fingerprint, the location where the information for the fingerprint was acquired is used to identify the current location of the instrument taking the procedure measurement in block 112.

A catheter can be used to introduce a lead, an ablation device, or other devices relative to the patient. The identified location of the catheter through the procedure 16 can be used to insure an appropriate positioning of the instrument during a procedure. Thus, a single catheter can be used for position identification and instrument placement.

After identifying and outputting the location, the procedure can end in block 126. Ending the procedure at block 126 can include other appropriate procedures, such as implanting a lead, performing an ablation procedure or other procedures.

It will be understood that the execution of the program in block 114 and the determination of the location of block 122 can be used to identify the location of any appropriate instrument within a patient or any other selected system. Further, positioning of the instrument can include positioning an instrument in any appropriate portion of the patient or mechanical system. Additionally, it will be understood that the one or more characteristics that are measured in block 112 can include measuring more than one characteristic at a particular location. For example, any two or more of a pulsative pressure, a motion (e.g. with an accelerometer), and an electrogram can be measured at a selected location in block 112. The multiple measured characteristics can then be compared to multiple different fingerprints to determine whether a match is found in block 116. This can allow for confirmation or increased possibility of location determination of the position of the instrument.

When more than one characteristic is measured, then larger amount of information can be used to make a location determination. For example, if two items (e.g. a motion fingerprint and a pulsative pressure fingerprint) are provided to identify a location, then the presence of both items can be used to identify the location. Thus, even if one item is present, but the other is not, a positive identification can be avoided.

It will be further understood that the fingerprint determined in block 50 and saved in block 60 can be a fingerprint that incorporates more than one characteristic for the data acquired in block 30. For example, the fingerprint can include two or more of motion information, pulsative pressure information, ECG information, and electrogram information. Thus, the fingerprints determined in block 50, therefore, need not be a fingerprint of a single characteristic that is measured at a particular location.

There can be two or more measurable characteristics at any specific location, such as within a superior vena cava, they can both be used to determine the fingerprint in block 50. The two characteristics can include pulsative pressure and motion. The two can be combined into a single finger print, such as a particular motion when a particular pulsative pressure is measured. Using multiple characteristics to generate a single fingerprint can allow for the determination of a particular or detailed fingerprint and for possibly more precise or certain identification of a position of an instrument.

As discussed above, the fingerprint is part of an identification routine for identifying a location of an instrument or device. When two or more measurements are taken they can be used to generate a procedure characteristic or procedure fingerprint. The procedure fingerprint can be generated similar to the training fingerprint, but based only on the measurement of the procedure location. When the procedure fingerprint includes more than one characteristic it can be more precisely and uniquely determined. The same is true for the training fingerprint. Thus, a match of the training fingerprint and the procedure fingerprint can be more difficult, but a match is more likely to a correct match and location identification.

Turning reference to FIG. 4, a patient 200 can have an instrument 202 positioned relative to a selected portion of the patient 200, such as a heart or cardiac region 204. The instrument 202 can be any appropriate instrument, such as a catheter 206 including a balloon or other portion 208 that can measure a characteristic. A sensor, such as a temperature sensor, can be positioned directly within the patient or, according to various embodiments, the balloon 208 can be used to amplify and transmit a pressure, including a pulsative pressure, to a processor and/or classifier system 210. The processor system 210 can include any appropriate processor system, such as within a workstation or other catheter control system. The instrument 202 can include a steerable portion, such that the catheter 206 can be a steerable catheter. Therefore, moving the catheter 206 through the patient 200 can be used for various procedures, such as implanting instruments or leads within the patient 200.

The processor system 210 can include human input portions, such as a mouse and keyboard 212 and a display device 214. The display device 214 can display various information regarding the measured characteristic in block 112, the outputted location from block 124, and other appropriate information, such as a certainty of the determined outputted location.

As discussed above, it will be understood that any appropriate characteristic can be measured in block 112. Accordingly, the display device 214 can include a measured characteristic indication 216. It will be further understood that various portions, such as a graphical user interface (GUI) can be used to alter, change, or add to the type of measured characteristic. The one or more measured characteristics can then be identified on the display device 214 in the display area 216.

The display device 214 can also include an instrument location output 218. The location output 218 can be any appropriate output, such as a word output or graphical output. For example, the word "superior vena cava" can be displayed on the display device 214 to identify the determined location of the instrument 206 within the patient 200. In addition, or alternative to the word output, a graphical illustration of the location of the instrument can also be displayed on the display device 214. For example, a model or stylized illustration of a heart or vasculature and an icon representing the location of the instrument can be displayed on the display device 214. In addition, or alternatively thereto, image data of the patient 200 can also be displayed on the display device 214 and an icon representing the location of the instrument 206 can be super-imposed on the display of the image data of the patient 200.

In addition, other information can be displayed regarding the procedure, such as the determination of the location of the instrument, in the patient 200. For example, a certainty level or percentage 220 can be illustrated on the display device 214. The certainty can include a calculation of the amount or certainty of the match between the procedure measured characteristic and the fingerprint.

A user, such as a surgeon, can base further or future actions based upon information outputted by the processor system 210. For example, the surgeon can decide to alter the type or number of characteristics being measured. Further, the surgeon can select to obtain more measurements or measure different types of characteristics to increase the certainty of the determined match. Regardless, the user can use the output on the display device 214 to gain knowledge of the location of the instrument 202 within the patient 200 after measuring a characteristic with the instrument.

It will be understood that the processor system 210 can either be a separate or single processor system with other processor systems. For example, the instrument 202 can be an ablation catheter or ablation system and the processor system 210 that executes the matching program in block 114 can be integrated into a control processor for the ablation instrument or can be a separate processor system that either is in communication with the ablation processor system or in communication with the instrument 202. Therefore, it will be understood, that the determination of the location of the instrument 202 can be used to assist in performing any appropriate procedure relative to the patient 200 or in any other appropriate system.

The fingerprint can be based on more than one characteristic. Also, a characteristic may be based on more than one type of measurement. Accordingly, a catheter or instrument can include more than one measuring sensor. Also, the fingerprint can be a rule defining whether a measurement is within a rule to identify a location. In addition, the system for classifying or identifying a match can be an algorithm or executable program that embodies the algorithm for classifying the procedure measurements.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system of determining a position of an instrument in a volume, comprising:
   a training instrument configured to be positioned exterior to a volume, wherein the training instrument is operable to obtain training data by collecting information regarding a characteristic in the volume;
   a classifier system configured to execute instructions to evaluate the training data and determine a classification of at least a portion of the volume based on the training data;
   a fingerprint determinative system configured to determine a fingerprint based at least on the determined classification of at least the portion of the volume; and
   a memory system to save at least one of the determined classification or the determined fingerprint;
   wherein at least one of the determined classification or the determined fingerprint is operable to identify at least the portion of the volume.

2. The system of claim 1, wherein the training instrument includes an imaging system configured to acquire image data of the volume.

3. The system of claim 2, wherein the imaging system is at least one of a computed tomography (CT) system, a magnetic resonance imaging (MRI) system, an ultrasound (US) system, a fluoroscopy system, or combinations thereof.

4. The system of claim 2, wherein the imaging system is non-invasive to the volume.

5. The system of claim 4, wherein the classifier system evaluates the training data to determine a density of at least a portion of the volume.

6. A system of determining a position of an instrument in a volume, comprising:
   a training instrument configured to be positioned exterior to a volume, wherein the training instrument is operable to obtain training data by collecting information regarding a characteristic in the volume and wherein the training instrument includes an imaging system configured to acquire image data of the volume;
   a classifier system configured to execute instructions to evaluate the training data and determine a classification of at least a portion of the volume based on the training data;
   a memory system to save the determined classification; and
   a fingerprint determinative system configured to determine a fingerprint based at least on the determined density of at least the portion of the volume wherein the determined classification is operable to identify at least the portion of the volume;
   wherein the imaging system is non-invasive to the volume.

7. The system of claim 6, further comprising:
   a memory system to store the fingerprint; and
   a comparative system configured to recall the saved fingerprint and compare the fingerprint to procedure data including a measured characteristic that is measured during a procedure.

8. The system of claim 7, further comprising:
   a procedure instrument configured to be positioned into a second volume to measure the characteristic in the second volume and obtain the procedure data;
   an output device to output a procedure location to a user;
   wherein the procedure location of the procedure instrument is determined based upon the comparative system comparing the fingerprint and the procedure data including the measured characteristic.

9. The system of claim 8, wherein the first volume and the second volume are the same volume.

10. A method of determining a position of an instrument in a volume, comprising:
    accessing training data collected with a training instrument positioned exterior to a volume,
    classifying the training data to determine a classification of at least a portion of the volume based on the training data;
    determining a fingerprint based at least on the determined classification of at least the portion of the volume; and
    storing at least one of the classification of the fingerprint with a memory system to save the determined classification;
    wherein at least one of the determined classification or the determine fingerprint is operable to identify at least the portion of the volume.

11. The method of claim 10, further comprising:
    accessing the training data including image data of the volume.

12. The method of claim 10, wherein classifying the training data includes executing instructions with a classifier system configured to evaluate the training data.

13. The method of claim 10, further comprising:
    evaluating procedure data with the classification; and
    determining a probability that the procedure data is acquired within at least the portion of the volume.

* * * * *

UNITED STATES PATENT AND TRADEMARK OFFICE
CERTIFICATE OF CORRECTION

PATENT NO. : 11,468,792 B2  Page 1 of 1
APPLICATION NO. : 16/997325
DATED : October 11, 2022
INVENTOR(S) : David A. Simon It is certified that error appears in the above-identified patent and that said Letters Patent is hereby corrected as shown below:

In the Specification

Column 14, Detailed Description, Line 22, Delete "206" and insert --202-- therefor Column 14, Detailed Description, Line 31, Delete "206" and insert --202-- therefor In the Claims Column 16, Line 33, In Claim 10, delete "volume," and insert --volume;-- therefor Signed and Sealed this
Twenty-second Day of August, 2023

Katherine Kelly Vidal
*Director of the United States Patent and Trademark Office*